United States Patent [19]

Schnur et al.

[11] Patent Number: 4,867,917

[45] Date of Patent: Sep. 19, 1989

[54] METHOD FOR SYNTHESIS OF DIACETYLENIC COMPOUNDS

[76] Inventors: Joel M. Schnur, 6009 Lincolnwood Ct., Burke, Va. 22015; Alok Singh, 6340 Rockshire St., Alexandria, Va. 22310

[21] Appl. No.: 946,440

[22] Filed: Dec. 24, 1986

[51] Int. Cl.$^4$ .............................................. C11C 1/00
[52] U.S. Cl. ................................. 260/413; 260/405.5
[58] Field of Search ............................. 260/405.5, 413

[56] References Cited

PUBLICATIONS

D. Mobius, *Acc. Chem. Res.*, 1981, vol. 14, 63.
Dejarlais, Emken, *Synthetic Commun.*, 1980, vol. 10, 653.
Singh et al., *Polymer Preprints*, vol. 26, 184–185.
Smith et al., *Synthesis*, 1974, 441.
Schnur et al., *Polymer Preprints*, vol. 26, 186 (9/85).
Bergel'son et al., *Zh. Obsh. Khim.*, 1962, vol. 32, 58.
Kovaleva et al., *Zh. Org. Khim.*, 1972, vol. 8, 2474.
Newton et al., *J. Chem. Res.*, (M), 1980, 3501.
Georger et al., *Polymer Preprints*, vol. 26, 207–208 (9/85).
Vaughn, *J. Amer. Chem. Soc.*, 1933, vol. 5, 3456.
Fendler, Monolayers and Organized Multilayer Assemblies in Membrane Mimetic Chemistry, 1982, 78.

*Primary Examiner*—Werren B. Lone
*Attorney, Agent, or Firm*—Wolf, Greenfield & Sacks

[57] ABSTRACT

A method for synthesizing a diynoic acid having the formula $CH_3(CH_2)_n—C\equiv C—C\equiv C—(CH_2)_mCO_2H$ comprising the steps of: selecting a one-halo alkyne from the group consisting of $CH_3(CH_2)_nC\equiv CX$, where X is a selected halogen; selecting an omega-alkynoic acid having the formula, $HC\equiv C(CH_2)_mCO_2H$; dissolving the alkynoic acid in an aqueous solution of base; adding a catalytic amount of cuprous halide dissolved in an aqueous solution of alkylamine to the aqueous solution of alkynoic acid; adding a reducing agent to the solution of alkynoic acid and cuprous halide; adding the one-halo alkyne to the solution; adding as much more of the reducing agent to the solution as is necessary to maintain the cuprous ion in the cuprous state; wherein m is selected from the group of 5, 6, 7, 8, 9, 10, and 11, and n is selected from the group of 7, 8, 9, 10, 11, 12, 13, 14, 15, and 16.

6 Claims, No Drawings

METHOD FOR SYNTHESIS OF DIACETYLENIC COMPOUNDS

U.S. GOVERNMENT RIGHTS IN THE INVENTION

This invention was made jointly by an employee of the Naval Research Laboratory, Washington, D.C. and an employee of Geo-Centers, Inc. The Geo-Centers employee, Dr. Alok Singh, at the time the invention was made, was in the performance of work under Naval Research Laboratory contract N00014-85-C-2243. The United States of America has certain rights in the invention arising out of that contract, including a nonexclusive, nontransferable, irrevocable, paid-up license to practice the invention or to have it practiced for or on behalf of the United States throughout the world. The United States of America may also have rights in the invention derived from the employee of the Naval Research Laboratory who is a joint inventor of this invention.

BACKGROUND OF THE INVENTION

The present invention relates to certain alkadiynoic species useful in the ultimate formation of certain phospholipid vesicles and a reproducible method for synthesizing such alkadiynoic species.

Previous attempts to synthesize diacetylene moieties within an alkyl chain have inevitably led to an indiscriminate and unpredictable mixture of various unsaturated isomers. The present invention provides a controllable and reproducible method for synthesizing diynoic acids having selected alkyl chain lengths. Such diacetylenic compounds are particularly useful in the synthesis of certain alkadiynoyl-sn-glycero-3 phospholipids and allow a polymerization thereof to form certain microstructures which are peculiarly stable in harsh physical and chemical environments.

SUMMARY OF THE INVENTION

In accordance with the invention there is provided a method for synthesizing a diynoic acid having the formula $CH_3(CH_2)_n-C\equiv C-C\equiv C-(CH_2)_m CO_2H$ comprising the steps of: selecting a one-halo alkyne from the group consisting of $CH_3(CH_2)_n C\equiv CX$, where X is a selected halogen; selecting an omega-alkynoic acid having the formula, $HC\equiv C(CH_2)_m CO_2H$; dissolving the alkynoic acid in an aqueous solution of base; adding a catalytic amount of cuprous halide dissolved in an aqueous solution of alkylamine to the aqueous solution of alkynoic acid; adding a reducing agent to the solution of alkynoic acid and cuprous halide; adding the one-halo alkyne to the solution; adding as much more of the reducing agent to the solution as is necessary to maintain the cuprous ion in the cuprous state; wherein m is selected from the group of 5, 6, 7, 8, 9, 10, and 11, and n is selected from the group of 7, 8, 9, 10, 11, 12, 13, 14, 15, and 16.

The cuprous halide is typically selected from the group of cuprous chloride, cuprous bromide and cuprous iodide. The temperature of the halo-alkyne, alkynoic acid reaction mixture is preferably maintained at or below about 25 degrees Centigrade and most preferably between about 14 and about 26 degrees Centigrade.

The one-halo alkyne is typically added in an amount about equimolar to the molar amount of the alkynoic acid; and, the one-halo alkyne is most preferably a one-iodo alkyne.

The amount of the alkylamine in the solution is typically maintained in an amount sufficient to maintain the cuprous halide completely dissolved in the aqueous solution.

The step of selecting the omega alkynoic acid typically comprises preparing the omega alkynoic acid by reaction of $Y-(CH_2)_m CO_2H$ with a Group IA cationic acetylide where Y is a selected halide. The Group IA acetylide is preferably selected from the group of sodium acetylide and lithium acetylide ethylenediamine.

Most preferably, the step of preparing the omega alkynoic acid comprises preparing a slurry of lithium acetylide ethylenediamine in dry solvent, adding about an equimolar amount of the $Y-(CH_2)_m CO_2H$ thereto and maintaining the mixture at a temperature of less than about 26 degrees Centigrade. The step of preparing the omega alkynoic acid preferably further comprises quenching the reaction mixture after less than about 3 hours with water and maintaining the mixture at between about 6 and about 12 degrees Centigrade during the quenching.

Alternatively the step of preparing the omega alkynoic acid may comprise dissolving sodium acetylide in a dry solvent slowly adding the $Y-(CH_2)_m CO_2H$ thereto and maintaining the reaction mixture at a temperature of less than about 26 degrees Centigrade. Y is preferably a bromo.

The cuprous halide which is added to the aqueous solution of alkynoic acid, is typically added in a molar amount of between about 0.1 and about 0.25 times the molar amount of alkynoic acid in the solution. The reducing agent is preferably a hydroxylamine hydrohalide and is added to the solution of between about 0.03 and about 0.05 times the molar amount of cuprous halide in the solution.

The alkylamine is preferably ethylamine.

The dry solvent utilized in the preparation of the omega alkynoic acid is typically selected from the group of diglyme, dioxane, dimethylformamide and dimethyl sulfoxide.

The one-halo alkyne may include a terminal group selected from the group of OH, 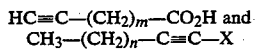 and $OCO(CH_3)C\equiv CH_2$.

DETAILED DESCRIPTION OF THE INVENTION

The basic heterocoupling reaction achieved herein is between:

$$HC\equiv C-(CH_2)_m-CO_2H \text{ and}$$
$$CH_3-(CH_2)_n-C\equiv C-X$$

where X is a selected halogen, preferably iodo, bromo or chloro (most preferably where X is an iodo), and where m is 5, 6, 7, 8, 9, 10, or 11 and where n is 7, 8, 9, 10, 11, 12, 13, 14, 15, or 16.

An omega alkynoic acid, $HC\equiv C-(CH_2)_m-CO_2H$ and a one halo alkyne $CH_3-(CH_2)_n-C\equiv C-X$ are first selected for use in producing a selected diynoic acid of the formula:

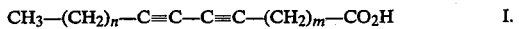

The following procedure produces such heretofore unknown diynoic species I in substantial field. The selected omega alkynoic acid is dissolved in an aqueous solution of base and a cuprous halide completely dissolved in an aqueous solution is added to the omega alkynoic acid. When adding the cuprous halide to the aqueous solution of omega alkynoic acid, the cuprous halide may precipitate out of solution due to insolubility in water. To avoid this result, the pre-prepared cuprous halide solution preferably comprises an excess of a solvent such as an alkylamine, typically ethylamine, which will maintain the cuprous halide completely dissolved in solution even after the pre-prepared cuprous halide solution is added to the aqueous omega alkynoic acid solution. The cuprous halide preferably comprises cuprous chloride, cuprous bromide, or cuprous iodide, typically cuprous chloride, and the total amount of cuprous halide added to the solution of omega alkynoic acid is preferably between about 0.1 and 0.25 times the total molar amount of omega alkynoic acid in the solution.

To the omega alkynoic acid/cuprous halide solution is added a reducing agent such as a hydroxylamine hydrohalide, most preferably hydroxylamine hydrochloride. The reducing agent is typically added initially in crystalline form, such as crystalline hydroxylamine hydrohalide, in a total amount of between about 0.03 and about 0.05 times the molar amount of cuprous halide in the solution.

To the above solution is next added the selected one-halo alkyne, preferably a one-iodo alkyne. The one-halo alkyne is typically pre-dissolved in a solvent which is compatible with the aqueous solution to which it is being added, such as methanol, ethyl ether and mixtures thereof. Preferably the one-halo alkyne is added in a total amount which is about equimolar to the molar amount of the omega alkynoic acid in the solution. The reaction temperature is preferably at all times maintained at such a point that isomerization of the dialkynoic product I does not occur. Preferably the reaction temperature is maintained at less than about 25 degrees Centigrade and most preferably between about 14 and about 26 degrees Centigrade. During and/or after the addition of the one-halo alkyne as much or more of the selected reducing agent is added to the solution as is necessary to maintain the copper ion in the cuprous (cu+) state; preferably the second addition of reducing agent is carried out by addition of the reducing agent pre-dissolved in a suitable solvent, such as a hydroxylamine hydrohalide, most preferably hydroxylamine hydrochloride dissolved in water.

The final reaction mixture is typically acidified with, for example, an aqueous hydrohalide solution and the alkadiynoic acid product I is extracted from the aqueous reaction mixture with an appropriate solvent such as ethyl ether, chloroform or the like.

The various omega alkynoic acids used in the heterocoupling reaction are typically pre-prepared. The preferred embodiments for preparing the selected alkynoic acid heterocoupling reactant involves the reaction of a group IA cationic acetylide with a selected omega halo alkanoic acid having the formula $Y-(CH_2)_mCO_2H$ where Y is a halide and m is 5, 6, 7, 8, 9, 10 or 11.

Most preferably lithium acetylide ethylenediamine complex (LAEDA) is selected as the acetylide reactant. LAEDA is typically added to a suitable dry solvent such as diglyme, dioxane, dimethyl sulfoxide or dimethyl formamide and a slurry is formed. The most preferred solvent is dimethyl sulfoxide. The reaction vessel containing the slurry is typically immersed in a cold bath maintained at less than about 5 degrees Centigrade and to the slurry is added the selected omega halo alkanoic acid which is typically pre-dissolved in a suitable dry solvent and added over less than about 3 hours to the slurry in an amount about equimolar to the molar amount of LEADA. The reaction mixture is preferably maintained at between about 4 and about 12 degrees Centigrade. Most preferably the concentration of LAEDA in the pre-prepared slurry is between about 1 and about 1.5 grams per 10 ml of dry solvent. The reaction mixture is preferably quenched by pouring the contents of the reaction vessel over crushed ice and stirring the contents which are preferably maintained at a temperature of between about 6 and about 12 degrees Centigrade. The quenched reaction mixture is preferably acidified with an aqueous hydrohalide solution and the omega alkynoic acid product extracted therefrom with an appropriate solvent such as hexane.

Alternatively, the selected omega alkynoic acid may be prepared by reaction of sodium acetylide with the selected omega halo alkanoic acid. Typically stored as a dispersion in mineral oil and xylene, the sodium acetylide is typically redispersed in a suitable dry reaction solvent such as dimethyl sulfoxide after removal of the mineral oil and xylene by washing with hexane. The selected omega halo alkanoic acid is typically added to the sodium acetylide solution (most preferably, dimethyl sulfoxide as solvent) and the reaction temperature is most preferably maintained at less than about 26 degrees Centigrade. Typically the reaction is quenched as described above after less than about 3 hours and worked up as described above with reference to the LAEDA reaction.

In both of above described preferred omega alkynoic acid preparation procedures, an omega bromo alkanoic acid is most preferred as a reactant.

The prepared alkadiynoic acids may be stored for periods of up to one year and longer in an anhydride form. Such anhydrides of such alkadiynoic acids are typically formed by reacting the acids with a carbodiimide preferably at around room temperature.

Following is a relatively specific and exemplary routine which may be followed to synthesize selected diynoic acids:

A selected molar amount of a selected alkynoic acid, $HC\equiv C(CH_2)_mCO_2H$, is dissolved in an aqueous 1.1 molar KOH solution. As much of a 0.25 molar solution of CuCl dissolved in a 70% ethylamine/water solvent is added to the alkynoic acid solution such tat the molar ratio of CuCl to alkynoic acid is between about 0.1 and about 0.25. To this solution is added as much crystalline hydroxylamine hydrochloride as is needed to achieve a ratio of cuprous chloride to hydroxylamine hydrochloride of between about 0.03 and about 0.05. A selected one-iodo alkyne, $I-C\equiv C(CH_2)_nCH_3$ dissolved in a 1:1 methanol-ethyl ether solvent is added slowly to the alkynoic acid/cuprous chloride solution until about an equimolar amount of iodoalkyne to alkynoic acid is attained. The temperature of the reaction mixture is maintained at between about 14 and about 26 degrees during the addition of the iodoalkyne. After the iodoalkyne is added, as much as of a 10% aqueous solution of hydroxylamine hydrochloride is added to the solution as is needed to maintain the copper ion in the solution in the cuprous state (solution typically turns yellow). All of the foregoing steps are carried out in about 15 minutes and the temperature of the reaction solution is maintained at less that about 26 degrees Centigrade during the addition of the selected iodoalkyne. Upon reaction of all of the iodoalkyne (yellow solution), the solution is acidified with a 30% HCl solution and extracted with ether. The ether is removed from the crude diynoic acid extract, the residue is chromatographed on an appropriate column of silica gel (eluted with chloroform), and the diynoic acid eluent is identified by conventional IR, NMR, MS, elemental analysis and melting point. Table I lists the analytical results of the performance of the foregoing synthetic procedure on selected omega alkynoic acids and one iodo alkynes.

TABLE I

| Example No. | m | n | DIYNOIC ACID YIELD (%) | MP °C. | Calculated % C | H |
|---|---|---|---|---|---|---|
| 1. | 5 | 11 | 39 | 68–69 | 79.46 | 10.9 |
| 2. | 5 | 13 | 20 | 70–71 | 79.95 | 11.7 |
| 3. | 5 | 16 | 37 | 60–61 | 82.6 | 11.8 |
| 4. | 6 | 13 | 42 | 64–66 | 80.15 | 11.3 |
| 5. | 6 | 15 | 49 | 68 | 82.6 | 11.8 |
| 6. | 7 | 9 | 56 | 49–50 | 79.46 | 10.91 |
| 7. | 7 | 14 | 51 | 53–55 | 82.6 | 11.8 |
| 8. | 9 | 12 | | 69–71 | | |
| 9. | 10 | 7 | 36 | 34 | 79.71 | 11.05 |
| 10. | 10 | 9 | 45 | 52–54 | 80.15 | 11.30 |
| 11. | 10 | 11 | 15 | 84–86 | 82.6 | 11.8 |
| 12. | 10 | 13 | 36 | 68–69 | 81.1 | 11.7 |
| 13. | 11 | 10 | | 68–69 | | |
| 14. | 11 | 13 | 54 | 61–62 | 81.1 | 11.78 |
| 15. | 8 | 10 | 27 | 61–64 | | |
| | \multicolumn{6}{l}{(OH, terminal; $HO_2C(CH_2)_m$—C≡C—C≡C—$(CH_2)_n$—OH) liquid} | |
| 16. | 8 | 10 | | 91 | | |
| | \multicolumn{6}{l}{($OCO(CH_3)C$=$CH_2$, terminal; $HO_2C(CH_2)_m$—C≡C—C≡C—$(CH_2)_n$—$OCO(CH_3)C$=$CH_2$)} | |
| 17. | 8 | 8 | 36 | 43–45 | | |
| | \multicolumn{6}{l}{($H_2C$=CH, terminal; $HO_2C(CH_2)_m$—C≡C—C≡C—$(CH_2)_n$—CH=$CH_2$)} | |

As shown in examples 15, 16, and 17 of Table I, the iodoalkyne reactant may include a terminal OH, $OCO(CH_3)C$=$CH_2$, or C=$CH_2$ group.

Following is an exemplary, relatively specific procedure for preparing a selected omega alkynoic acid reactant, $HC{\equiv}C(CH_2)_mCO_2H$, for use in the diynoic acid synthesis.

An appropriate reaction vessel is fitted with a nitrogen inlet and outlet. A slurry of a selected amount of lithium acetylide ethylenediamine complex in dry dimethyl sulfoxide (1–1.5 g LAEDA per 10 ml DMSO) is placed in the reaction vessel. The reaction vessel is placed in a cold bath maintained at about 4 degrees Centigrade and to the slurry is slowly added over about 15 minutes an amount of a selected omega bromo alkanoic acid, Br—$(CH_2)_mCO_2H$ (dissolved in dry DMSO) which is approximately equal to the selected molar amount of LAEDA in the slurry. The reaction mixture is stirred for less than about 3 hours after the omega bromo alkanoic acid addition is complete and the reaction temperature is maintained at between about 6 and about 12 degrees Centigrade at all times during and after the completion of the addition of the omega bromo alkanoic acid. The reaction mixture is quenched by pouring the contents of the reaction vessel on crushed ice and stirring. The quenched reaction mixture is acidified with a 10% HCL solution, the crude alkynoic acid product is extracted with hexane and the extracts are washed with water and dried over anhydrous $MgSO_4$. The omega alkynoic acid product is recovered by removing the ether and vacuum distilling of the residue. The homogeneity of the omega alkynoic acid distillation product is checked by conventional gas chromatography and characterized by conventional IR and NMR.

Alternatively, the selected omega alkynoic acid reactant may be prepared by the use of sodium acetylide. Typically, a selected molar amount of sodium acetylide reagent stored in xylene and mineral oil is washed with ether to remove the xylene and mineral oil. The ether is removed and the sodium acetylide is redispersed in an appropriate reaction vessel in dry dimethyl sulfoxide. The reaction vessel is immersed in a cold bath maintained at about 4 degrees Centigrade. Approximately an equimolar amount of the selected omega bromo alkanoic acid is added to the sodium acetylide reagent and reacted and worked up in the same manner as described above with reference to LAEDA.

The alkadiynoic acids so obtained are typically stored for later use by conversion to their anhydride forms which do not polymerize. A typical anhydride formation reaction comprises reacting the isolated acids with dicyclohexyl carbodiimide (0.55 molar in carbon tetrachloride) at room temperature. The acids are typically recovered for later use by redispersing the anhydrides in chloroform and passing the solution through a column of silica gel.

It will now be apparent to those skilled in the art that other embodiments, improvements, details, and uses can be made consistent with the letter and spirit of the foregoing disclosure and within the scope of this patent, which is limited only by the following claims construed in accordance with the patent law, including the doctrine of equivalents.

What is claimed is:

1. A method for synthesizing a diynoic acid having the formula $CH_3(CH_2)_n$—C≡C—C≡C—$(CH_2)_mCO_2H$ comprising the steps of:
    selecting a one-halo alkyne from the group consisting of $CH_3(CH_2)_nC{\equiv}CX$, where X is a halogen;
    preparing an omega alkynoic acid by reacting Y—$(CH_2)_mCO_2H$ with a Group IA cationic acetylide where Y is a halide;
    dissolving the alkynoic acid in an aqueous solution of base;
    adding a catalytic amount of cuprous halide selected from the group consisting of cuprous chloride, cuprous bromide and cuprous iodide dissolved in an aqueous solution of alkylamine to the aqueous solution of alkynoic acid;
    adding a reducing agent to the solution of alkynoic acid and cuprous halide;
    adding the one-halo alkyne to the solution;
    adding as much more of the reducing agent to the solution as is necessary to maintain the cuprous ion in the cuprous state, the temperature of the halo alkyne, alkynoic acid reaction mixture being maintained between about 14 and about 26 degrees Centigrade;
    wherein m is selected from the group of 5, 6, 7, 8, 9, 10, and 11, and n is selected from the group of 7, 8, 9, 10, 11, 12, 13, 14, 15, and 16.

2. The method of claim 1 wherein the Group IA acetylide is selected from the group of sodium acetylide and lithium acetylide ethylenediamine.

3. The method of claim 2 wherein the step of preparing the omega alkynoic acid comprises preparing a slurry of lithium acetylide ethylenediamine in dry solvent, adding about an equimolar amount of the Y—$(CH_2)_m CO_2H$ thereto and maintaining the mixture at a temperature of less than about 26 degree Centigrade.

4. The method of claim 3 wherein the step of preparing the omega alkynoic acid further comprises quenching the reaction mixture after less than about 3 hours with water and maintaining the mixture at between about 6 and about 12 degree Centigrade during the quenching.

5. The method of claim 2 wherein the step of preparing the omega alkynoic acid comprises dissolving sodium acetylide in a dry solvent, slowly adding the Y—$(CH_2)_m CO_2H$ thereto and maintaining the reaction mixture at a temperature of less than about 26 degrees Centigrade.

6. The method of claim 5 wherein the step of preparing the omega alkynoic acid further comprises quenching the reaction mixture after less than 3 hours with water and maintaining the mixture at between about 6 and about 12 degrees Centigrade during the quenching.

* * * * *